(12) United States Patent
Watson

(10) Patent No.: US 6,502,699 B1
(45) Date of Patent: Jan. 7, 2003

(54) METHOD AND KIT FOR MAKING INJECTIONS AND WITHDRAWING BLOOD WITHOUT THE USE OF PROTECTIVE GLOVES

(76) Inventor: Robert L. Watson, 1704 Singletree, Bowling Green, KY (US) 42103

( * ) Notice: Subject to any disclaimer, the term of this patent is extended or adjusted under 35 U.S.C. 154(b) by 21 days.

(21) Appl. No.: 09/784,745

(22) Filed: Feb. 15, 2001

Related U.S. Application Data

(60) Provisional application No. 60/212,991, filed on Jun. 21, 2000.

(51) Int. Cl.[7] .............................................. B65D 71/00
(52) U.S. Cl. ..................................... 206/571; 206/570
(58) Field of Search ................................ 206/364, 438, 206/570, 571, 363, 365

(56) References Cited

U.S. PATENT DOCUMENTS

| | | | | |
|---|---|---|---|---|
| 4,262,800 A | * | 4/1981 | Nethercutt | 206/364 |
| 4,300,567 A | | 11/1981 | Kolenik et al. | |
| 4,446,970 A | * | 5/1984 | Further | 206/223 |
| 4,886,071 A | * | 12/1989 | Mehl et al. | 206/366 |
| 4,954,239 A | * | 9/1990 | Mueller | 206/210 |
| 5,117,981 A | * | 6/1992 | Crawford et al. | 206/370 |
| 5,520,041 A | * | 5/1996 | Haswell | 73/29.04 |
| 5,569,225 A | | 10/1996 | Fleury | |
| 5,725,566 A | | 3/1998 | Pioger et al. | |
| 5,728,071 A | | 3/1998 | Watson et al. | |
| 5,738,641 A | | 4/1998 | Watson et al. | |
| 5,792,102 A | | 8/1998 | Muller-Spath | |
| 6,065,659 A | * | 5/2000 | Faz | 206/570 |
| 6,159,243 A | | 12/2000 | Schouwenburg | |
| 6,206,871 B1 | | 3/2001 | Zanon et al. | |
| 6,264,619 B1 | * | 7/2001 | Ferguson | 206/569 |

* cited by examiner

*Primary Examiner*—David T. Fidei
(74) *Attorney, Agent, or Firm*—James Daly, IV; Joan L. Simunic; Middleton Reutlinger

(57) ABSTRACT

A sterilized supply kit that provides the medical practitioner with the accessories necessary for marking an injection or withdrawing blood from a patient, or both. The kit includes one or more sterilizing agents, needles, syringes, fluid collection tubes, and absorbent pads. The absorbent pads are designed to cover the sight of skin puncture and create a bodily fluid barrier that makes the use of gloves to protect the practitioner unnecessary. The kit may additionally contain a tourniquet, a sterile sheet and/or medication to be administered. All the components of the kit are contained within a sterile sealable packet.

10 Claims, 4 Drawing Sheets

METHOD AND KIT FOR MAKING INJECTIONS AND WITHDRAWING BLOOD WITHOUT THE USE OF PROTECTIVE GLOVES

CROSS-REFERENCE TO RELATED APPLICATIONS

This application claims priority from U.S. Provisional Application Ser. No. 60/212,991, filed Jun. 21, 2000, which application is incorporated herein by reference in its entirety.

BACKGROUND

The present invention relates to a method that allows the medical practitioner to make injections through a patient's skin or to withdraw blood from a blood vessel without the need for the practitioner to wear protective apparel while performing these functions, and to a supply kit that provides the practitioner with the accessories necessary for the injection or blood withdrawal procedure.

Although the procedure for making injections or withdrawing blood appears relatively simple when performed by those skilled in the art, the actual procedure requires the use of several small items which must all be present at a single location at a specific time. For example, typically when an injection is to be made, the patient's skin must be cleansed with a disinfecting agent, such as an alcohol wipe; then a second disinfecting agent, such as iodine or Betadine may be applied to the skin; the needle must be attached to an appropriate syringe, the syringe filled with the proper medication, and the needle injected through the patient's skin so the medication can be delivered subcutaneously or intravenously; the needle must then be removed and wiped clean; and the puncture site must be covered with an absorbent pad until after hemostasis. Further, for the patient's protection, all the items must remain sterile prior to use. Similar steps are followed when blood is being withdrawn from a patient except that an area is usually isolated with a tourniquet to restrict the blood flow within the artery or vein making the vessel more visible before the needle is inserted, and the needle is attached to a collection device, such as a vacutainer tube, instead of a syringe.

Overall, a seemingly simple procedure requires the practitioner to manipulate numerous small items in a very short time period. If the practitioner or other members of the medical team must gather these items from separate locations, considerable time can be consumed and the cost to the patient can be relatively high because the medical staff must use valuable time on essentially non-medical activities. Further, there is a risk that one or more items may not be properly gathered causing additional delays.

Thus, it would be beneficial to have a sterilized kit containing all necessary items for the injection or blood withdrawal procedure which the practitioner could open when needed. Having the kits pre-assembled would ensure that all necessary components were available when needed; would save valuable time for the practitioner and medical staff with respect to assembly functions, thereby giving them more time to focus on the critical aspects of the procedure, such as to confirm medication type and dosage; and would provide a cost savings to the patient because lower assembly cost methods could be used to prepare the kits in advance rather than paying medical labor costs for the performance of non-medical functions.

SUMMARY OF THE INVENTION

The present invention relates to a sterilized supply kit that provides the medical practitioner with the accessories necessary for making an injection or withdrawing blood from a patient. The kit allows the practitioner to have all necessary supplies in one location, and the kit is appropriately sealed so that it remains sterile until opened for use. In the preferred embodiment, the kit contains items that also allow the practitioner to make injections through a patient's skin or to withdraw blood from a blood vessel without the need for the practitioner to use protective apparel while performing these functions.

DETAILED DESCRIPTION OF THE PREFERRED EMBODIMENT

The present invention is for a sterilized supply kit that provides the medical practitioner with the accessories necessary for making an injection to or withdrawing bodily fluids from a patient. By having the accessories included in a single kit, the practitioner can better serve the patient by being sure that everything is at the necessary location at the required time. Further, the kit can be maintained sterile until needed, thereby reducing the risk of infection to the patient.

Figure 1:
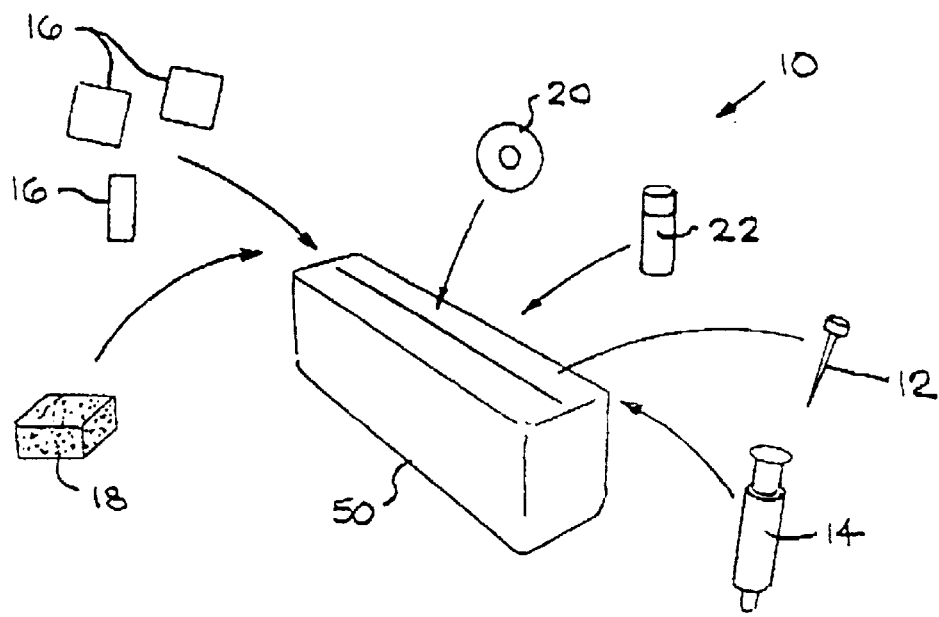
FIG. 1 is an exploded perspective view of an injection kit of the present invention.

In a first embodiment of the kit, shown in FIG. 1, the accessories included are specifically designed to allow the practitioner to make an injection. Generally, the injection kit 10 includes a needle 12 and syringe 14, sterilizing agents 16 and a sponge 18, and an absorbent pad 20 that can be secured to the patient's skin, all contained within a sealed packet 50. Optionally, the injection kit can include the medication 22 to be injected into the patient. When an injection is to be made, the practitioner opens the sealed kit; cleans the injection site with one or more of the sterilizing agents; attaches the needle to the syringe; fills the syringe from a medication vial, if necessary; injects the needle through the patient's skin and injects the medication; withdraws the needle from the skin; covers the puncture site with the absorbent pad; and discards the needle and syringe.

The selection of needle and syringe may vary as necessary for kits for different applications. One recommended combination is a 22-guage needle and a 3-mL syringe, such as are typically used for injections, but other combinations may be used as appropriate, and the suggested combination is not intended to be limiting. Optionally, the needle 12 may include a protective sleeve, as is known in the art, where the needle is protected before use and into which the needle can be withdrawn after use, thereby protecting the user from possible pricks. The selection of disinfecting agents and means for applying the disinfectants to the patient's skin may also vary depending on the intended specific use for the kit. Some typical disinfecting agents include rubbing alcohol, iodine, and Betadine, which may or may not be provided with application pads in individually sealed packets, but other agents and means for application may be included as appropriate. The post-injection bleeding patch can also vary from a relatively simple gauze pad plus adhesive strips, to a bandage, to a patch specifically designed to contain blood from an injection site, such as the injection pad described in U.S. Pat. No. 5,728,071 and incorporated herein by reference, or may be any other combination of components that allows the practitioner to cover the puncture site with an absorbent material and to hold that material at the puncture site. Optionally, the medication to be injected into the patient may be included in the kit, and may be supplied in a vial, ampule, bottle, pre-filled syringe, or similar medication storage container. For example, some typical medications which could be supplied in the injection kit would be vaccines, commonly used antibiotics, or similar commonly medications, as is known in the art.

In a preferred embodiment of the injection kit, the absorbent pad is a post-injection bleeding patch described in U.S. Pat. No. 5,728,071. When using this patch the injection procedure varies slightly from that described above in that the practitioner opens the sealed kit; cleans the injection site with one or more of the sterilizing agents; applies the patch to the patient's skin; attaches the needle to the syringe; fills the syringe from the medication vial; injects the needle through the injection patch and through the patient's skin and injects the medication; withdraws the needle from the skin and the patch; and discards the needle and syringe.

Selection of the specially designed '071 injection patch as the absorbent pad is recommended because, in recent years, it has been officially and widely recognized that blood-borne pathogens are an important and serious method of transmission of infectious diseases. Health care workers in particular are in danger from such exposure, but the danger exists for any person who is likely to come in contact with the blood of a person who is infected with such a disease. Obviously, when an injection is being made, or when blood is being withdrawn, the medical practitioner risks exposure to the patient's blood. The Occupational Safety and Health Administration (OSHA) and Center for Disease Control (CDC) have recommended that all human blood and other potentially infectious materials be treated as if known to be infectious for HIV, HBV or other blood-borne pathogens regardless of the perceived low risk of a patient or patient population. Thus, practitioners have been advised to wear protective apparel, such as latex gloves, whenever an injection is being made or when blood is being withdrawn. However, the protective apparel can be uncomfortable, may cause rashes or skin irritations for the practitioner, and can make it difficult for the practitioner to perform the necessary tasks because the gloves tend to stick to the adhesives used to hold bandages and similar skin patches in position against the patient's skin.

By using the injection patch of the '071 patent the practitioner can eliminate the need for protective apparel because these patches are applied to the skin before the needle enters the skin, they facilitate needle injection through the patient's skin, confine blood from the injection wound within the absorbent pad placed and held against the skin of a patient around an intended injection site, and the patch cleanses the needle as it is removed from the patient's skin, so the practitioner is not directly exposed to the patient's blood. Specifically, the patch includes an elastomeric, self-sealing membrane through which the needle penetrates to enter the patient's skin. Blood from the puncture site is confined within the covered patch region during the injection. When the needle is withdrawn, the membrane wipes the needle so essentially no blood is removed from the patch. The membrane then holds the absorbent pad close to the patient's skin to contain blood from the injection site until after hemostasis. Thus, the patient's blood is confined and the practitioner does not need to wear protective gloves while making the injection.

Figure 2:
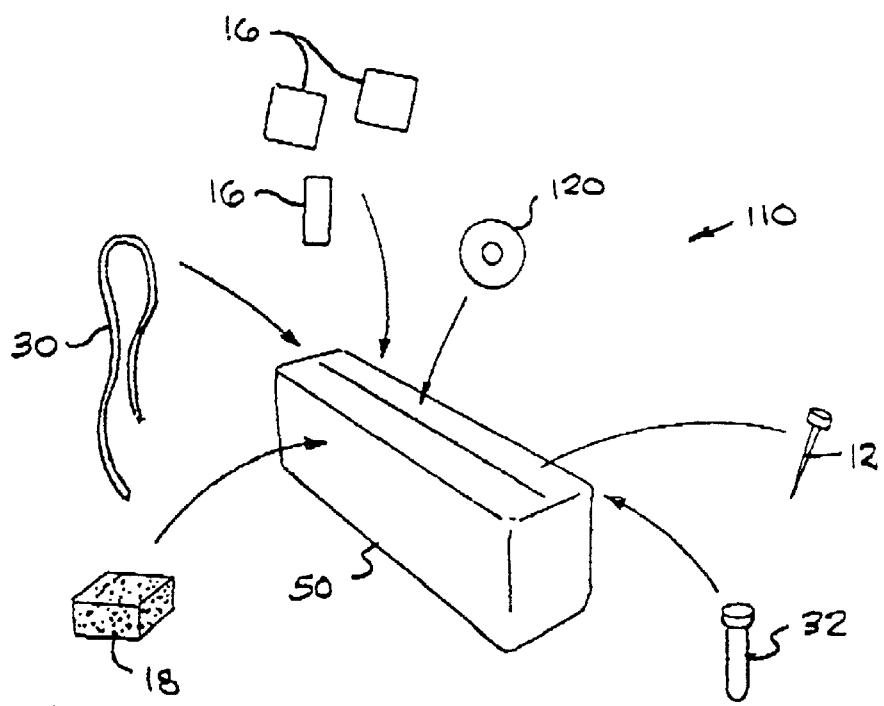
FIG. 2 is an exploded perspective view of a blood withdrawal kit of the present invention.

In a first alternative embodiment of the kit 110, shown in FIG. 2, the accessories included are specifically designed to allow the practitioner to withdraw bodily fluids, such as blood or tissue fluid, from the patient, and are generally similar to the accessories of the injection kit except that a tourniquet 30 is included in the kit and a collection tube 32 replaces the syringe. When a blood draw is to be made, the practitioner opens the sealed kit; isolates a selected region of the patient's body, such as the lower arm, with the tourniquet to restrict the blood flow within the region and make the blood vessels more visible; cleans the injection site with one or more of the sterilizing agents; attaches the needle to the collection tube; injects the needle into the patient's blood vessel and collects the blood sample in the tube; withdraws the needle from the skin; covers the puncture site with the absorbent pad; discards the needle and labels the tube for analysis. If a tissue fluid draw is to be made, the practitioner may elect to eliminate the isolation step and can withdraw fluid directly from the edematous area.

The selection of needle and syringe may vary as necessary for kits for different applications. One recommended combination is a 23-guage needle that can be securely attached to a standard vacutainer insertion tube, such as are typically used for blood collections, but other combinations may be used as appropriate, and the suggested combination is not intended to be limiting. The selection of disinfecting agents and means for applying the disinfectants to the patient's skin may also vary depending on the intended specific use for the kit. Some typical disinfecting agents include rubbing alcohol, iodine, and Betadine, which may or may not be provided with application pads in individually sealed packets, but other agents and means for application may be included as appropriate. The post-injection bleeding patch can also vary from a relatively simple gauze pad plus adhesive strips, to a bandage, to a patch specifically designed to contain blood from a withdrawal site, such as the withdrawal patch described in U.S. Pat. No. 5,738,641 and incorporated herein by reference, or may be any other combination of components that allows the practitioner to cover the puncture site with an absorbent material and to hold that material at the puncture site. As with the injection kit, the use of the '641 withdrawal patch is highly recommended, though not required, because the patch covers the puncture site before blood is present and removes the blood from the needle as it is removed from the patient's skin, thereby allowing the practitioner to eliminate the use protective apparel, if desired.

Figure 3:
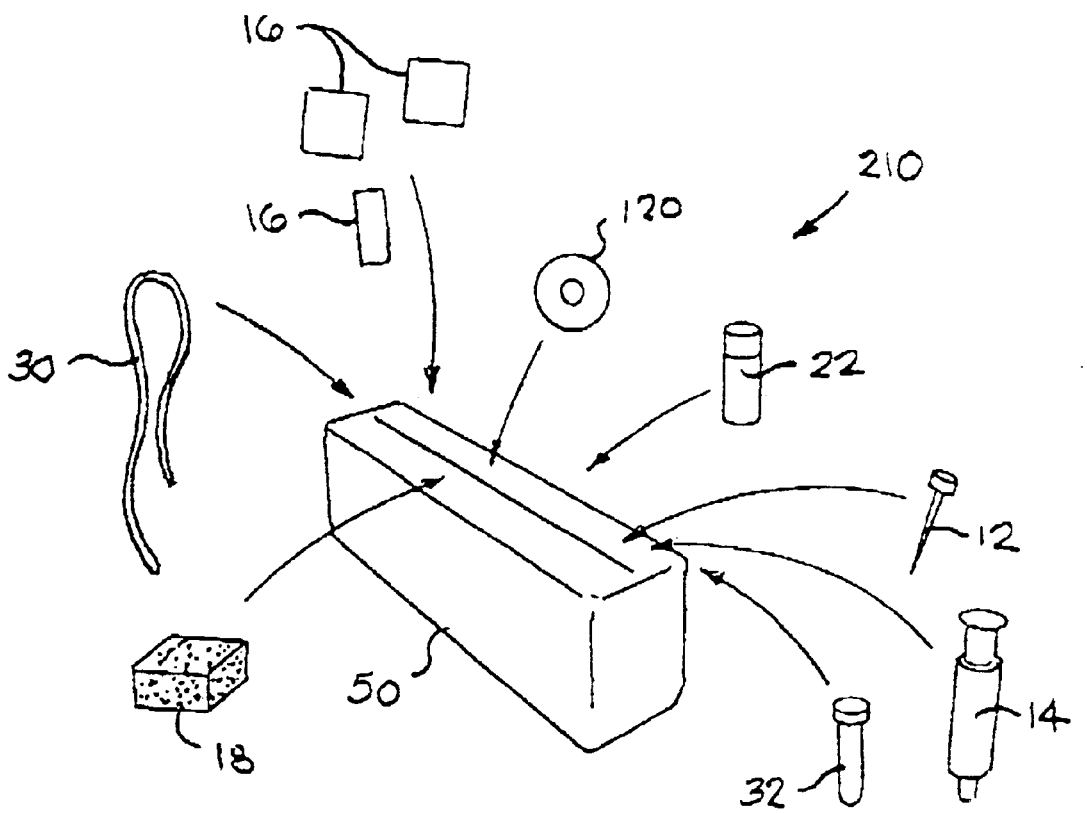
FIG. 3 is an exploded perspective view of a combination kit of the present invention.

A second alternative embodiment of the kit 210, shown in FIG. 3, includes all the accessories to allow the practitioner to make a blood withdrawal, but further includes a syringe 14, so the same kit could be used for an injection procedure. In use, the practitioner would select those items necessary for the specific injection or blood-withdrawal procedure and would follow the methods as described above. The advantages of having a combination kit is that the difference in assembly cost is nominal, but the medical center would not need to keep an inventory of separate kits, and the practitioner would not need to confirm that the proper kit—injection or blood withdrawal—had been obtained before the kit was opened. If the '641 patch is included in the kit as the absorbent pad, then there is no need to also include the '071 patch, as the '641 patch performs all the functions of the '071 patch and adds an additional measure of protection for the practitioner.

Figure 4:
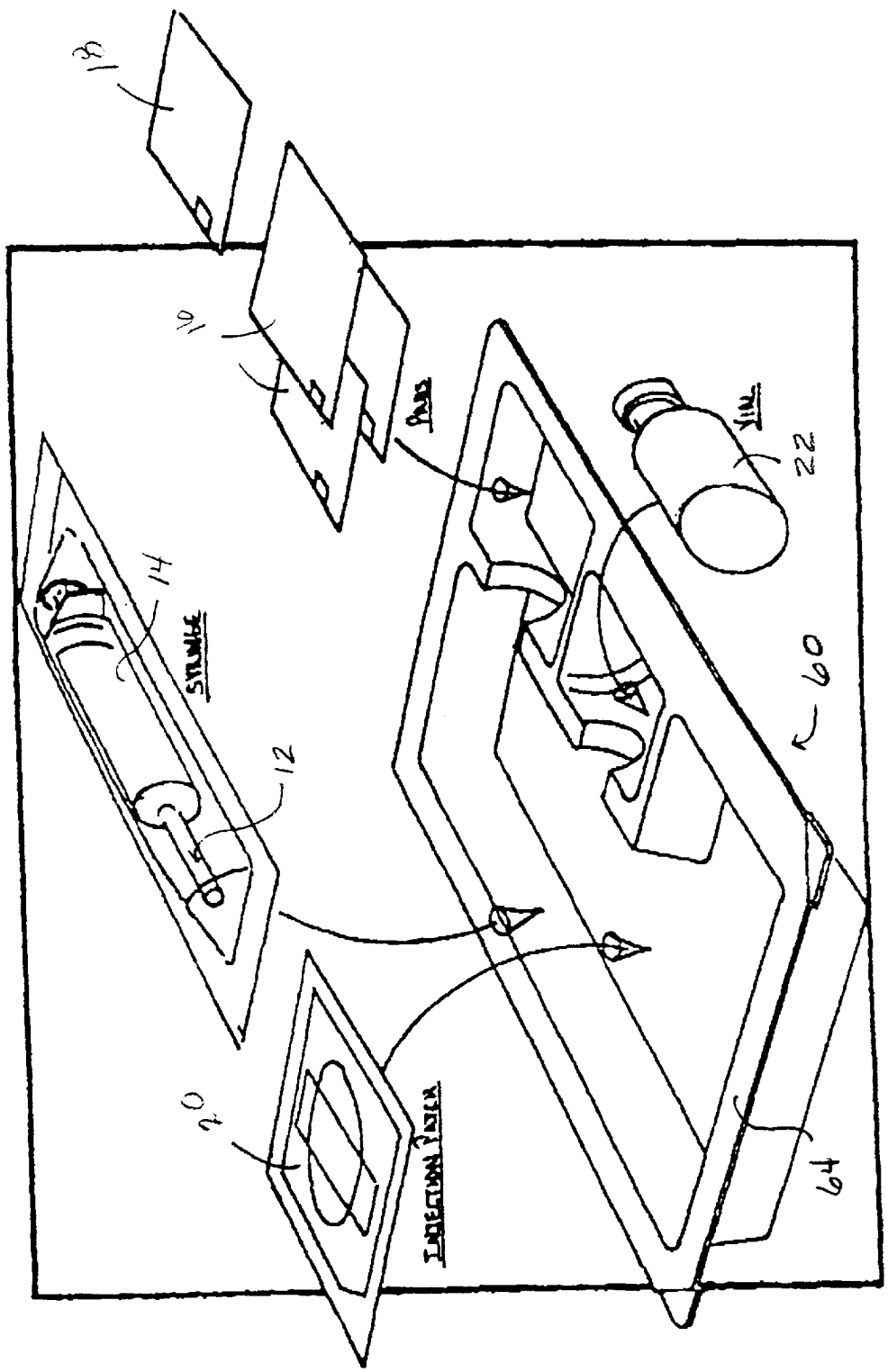
FIG. 4 is a perspective view of an injection kit of the present invention using a tray to hold the accessories.

For the injection kit 10, the blood withdrawal kit 110, and the combination kit 210, all accessories—needles, syringes, tubes, sterilizing agents, absorbent pads, tourniquets, medications, as appropriate for the specific kit—are contained within a sealed packet 50 and are sterilized as an extra measure of protection for the patient, thus, reducing the risk of infection. The sealed packet 50 may have a variety of forms, such as a blister pouch, a shrink wrapped pouch, a vacuum sealable pouch, a sealable thermoformed tray, or a similar pouch or tray form, with the accessories loosely packed within the pouch. For example, FIG. 4 shows a thermoformed tray 60 designed to hold all accessories for the injection kit 10, the blood withdrawal kit 110, or the combination kit 210. If the thermoformed tray is used for the injection kits 10, 210, a medication vial 22 can be included in the kit, and preferably, the tray 60 is molded to snuggly hold 1cc, 5cc, or 10cc vials or ampules, as are commonly used for medications delivered by injection. The tray 60 is preferably covered and sealed with a polymeric sheet (not shown) adhered to the edges 62 of the tray 60. The sheet can adhered to the tray 60 by any of a variety of known techniques, such as gluing, adhesives, heat sealing, or combinations thereof. Preferably, the kit is sterilized after the accessories are added to the pouch, thereby allowing the individual accessories in the pouch to be otherwise unwrapped, reducing packaging costs overall and minimizing the time required by the practitioner when using the kit because the individual components do not need to be unwrapped before use. The kits can be sterilized using any appropriate sterilization techniques, such as radiation sterilization, heat sterilization, or other sterilization methods known in the art.

Figure 5:
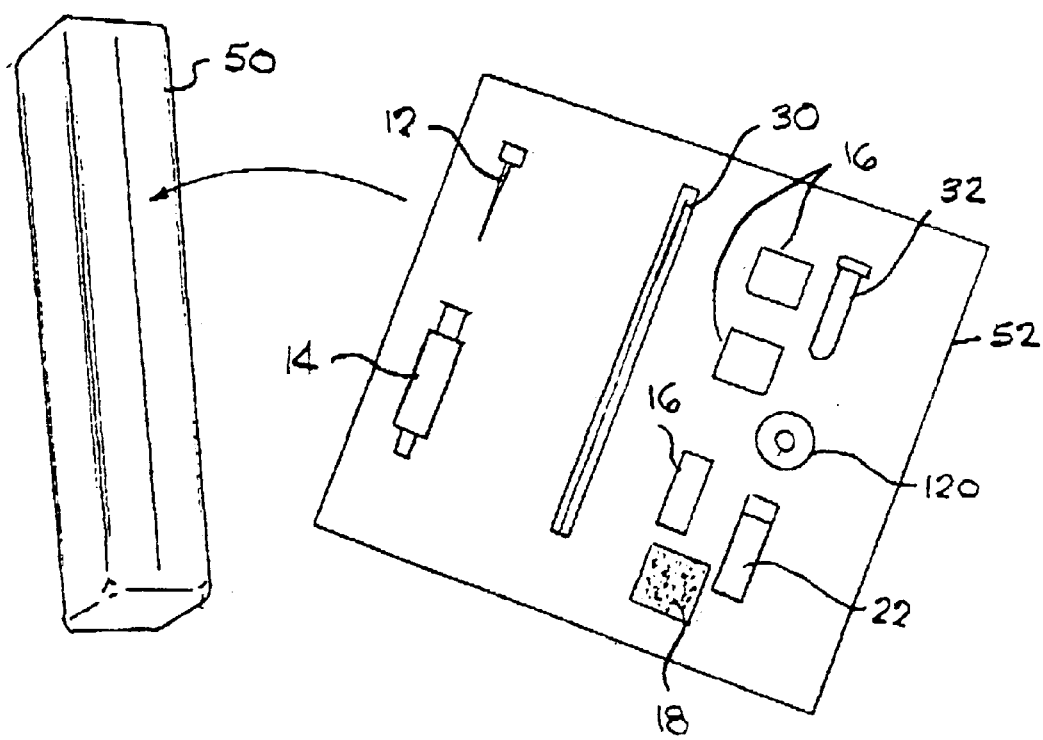
FIG. 5 is a first alternative embodiment of the combination kit of FIG. 3 further including an adhesive sheet.
Figure 5A:
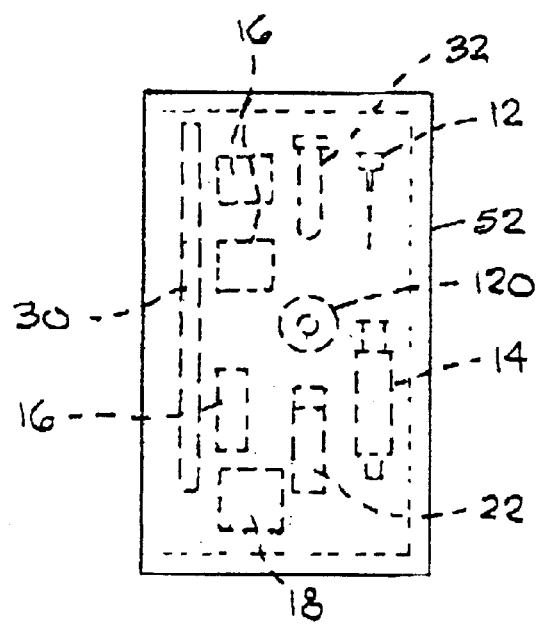
FIG. 5A is a second alternative embodiment of the combination kit wherein the adhesive sheet forms the packet.

Optionally, as shown in FIG. 5, the packet 50 may further include a protective sheet 52 made of cloth, tissue, a polymeric material sheet, or combinations thereof, to which the accessories may be loosely adhered, preferably in the expected order of use. The accessories may be held onto the sheet 52 using any of a variety of adhesives which are known in the art. After the accessories are positioned on the sheet 52, the sheet 52 can be either folded or rolled, sealed, and sterilized. The protective sheet 52 may be separate from the packet 50, as shown in FIG. 5, or as shown in FIG. 5A, it may be a liner for the packet 150, such that when the packet 150 is opened the protective sheet 152 is opened at the same time. For example, the kit 510 may include a sheet 152 having a polymeric layer backing 154 and a tissue-like non-woven polymeric top layer 156; the accessories may then be positioned on and held to the top layer of the sheet using an ambient temperature tacky adhesive—as is known in the art; the sheet 152 is then folded essentially in half, with the accessories contained within the folds of the sheet; the sheet is heat sealed along the open edges; and the sealed sheet with accessories is then sterilized by subjecting the assembled kit to a radiation treatment. To use the kit, the practitioner merely tears the edges from the sheet, and opens the sheet out on any surface, thereby allowing the practitioner to have all the accessories in one location, in the common order of use, and with minimum risk of having one or more accessories fall to the ground as the kit is being opened.

It is understood that, in light of a reading of the foregoing description and drawings, those with ordinary skill in the art will be able to make changes and modifications to the present invention without departing from the spirit or scope of the invention, as defined herein.

What is claimed is:

1. A sterilized injection kit allowing a medical practitioner to puncture a patient's skin and to inject a medication into the patient, said kit containing:
   a. at least one sterilizing agent, supplied such that the agent can be used to cleanse the patient's skin at the intended puncture site;
   b. at least one needle, to be used to puncture the patient's cleansed skin;
   c. at least one syringe, adapted to attach securely to said needle before the patient's skin is punctured;
   d. at least one absorbent pad, adapted to adhere to the patient's skin and cover the puncture site, said absorbent pad being a post-injection bleeding patch having an elastomeric, self-sealing membrane through which said needle can be inserted and injected into the patient's skin; and
   e. a sealable packet of sufficient size to contain said sterilizing agent, said needle said syringe, and said absorbent pad prior to use by the medical practitioner.

2. The injection kit of claim 1 further including a container containing a preselected medication to be injected into the patient through the puncture site, said medication container fitting within said packet prior to use.

3. A sterilized fluid withdrawal kit allowing a medical practitioner to puncture a patient's skin and to withdraw bodily fluid from the patient, said kit containing;
   a. at least one sterilizing agent, supplied such that the agent can be used to cleanse the patient's skin at the intended puncture site;
   b. at least one needle, to be used to puncture the patient's cleansed skin;
   c. at least one fluid collection tube; adapted to attach securely to said needle before the patient's skin is punctured;
   d. at least one absorbent pad, adapted to adhere to the patient's skin and cover the puncture site, said absorbent pad being a withdrawal patch having an elastomeric, self-sealing membrane through which said needle can be inserted and injected into the patient's skin; and
   e. a sealable packet of sufficient size to contain said sterilizing agent, said needle said collection tube, and said absorbent pad prior to use by the medical practitioner.

4. The fluid withdrawal kit of claim 3 further including a tourniquet, for restricting blood flow within a selected region of the patient's body prior to puncturing the skin with said needle, said tourniquet fitting within said packet prior to use.

5. A sterilized skin puncture kit allowing a medical practitioner to puncture a patient's skin and to either inject a medication or withdraw bodily fluid from the patient, said kit containing:
   a. at least one sterilizing agent, supplied such that the agent can be used to cleanse the patient's skin at the intended puncture site;
   b. at least one needle, to be used to puncture the patient's cleansed skin;
   c. at least one syringe, adapted to attach securely to said needle before the patient's skin is punctured;
   d. at least one fluid collection tube, adapted to attach securely to said needle before the patient's skin is punctured;
   e. at least one absorbent pad, adapted to adhere to the patient's skin and cover the puncture site, said absorbent pad being a withdrawal patch having an elastomeric, self-sealing membrane through which said needle can be inserted and injected into the patient's skin; and f. a sealable packet of sufficient size to contain said sterilizing agent, said needle said syringe, said collection tube, and said absorbent pad prior to use by the medical practitioner.

6. The skin puncture kit of claim 5 further including a tourniquet, for restricting blood flow within a selected region of the patient's body prior to puncturing the skin with said needle, said tourniquet fitting within said packet prior to use.

7. The skin puncture kit of claim 5 further including a container containing a preselected medication to be injected into the patient through the puncture site, said medication container fitting within said packet prior to use.

8. A sterilized skin puncture kit allowing a medical practitioner to puncture a patient's skin and to either inject a medication or withdraw bodily fluid from the patient, said kit containing:

a. at least one sterilizing agent, supplied such that the agent can be used to cleanse the patient's skin at the intended puncture site;

b. at least one needle, to be used to puncture the patient's cleansed skin;

c. at least one syringe, adapted to attach securely to said needle before the patient's skin is punctured;

d. at least one fluid collection tube, adapted to attach securely to said needle before the patient's skin is punctured;

e. at least one absorbent pad, adapted to adhere to the patient's skin and cover the puncture site, said absorbent pad being a withdrawal patch having an elastomeric, self-sealing membrane through which said needle can be inserted and injected into the patient's skin;

f. a sheet, adapted to loosely adhere said sterilizing agent, said needle said syringe, said collection tube, and said absorbent pad; and g. a sealable packet of sufficient size to contain said sterilizing agent said needle, said syringe, said collection tube, and said absorbent pad prior to use by the medical practitioner.

9. The skin puncture kit of claim 8 further including a tourniquet, for restricting blood flow within a selected region of the patient's body prior to puncturing the skin with said needle, said tourniquet being loosely adhered to said sheet prior to use.

10. The skin puncture kit of claim 8 further including a container containing a preselected medication to be injected into the patient through the puncture site, said medication container being loosely adhered to said sheet prior to use.

* * * * *